United States Patent
Kuwabara

[11] Patent Number: 5,978,442
[45] Date of Patent: Nov. 2, 1999

[54] FLUORESCENT X-RAY SPECTROSCOPES

[75] Inventor: Shoji Kuwabara, Osaka, Japan

[73] Assignee: Shimadzu Corporation, Kyoto, Japan

[21] Appl. No.: 09/010,257

[22] Filed: Jan. 21, 1998

[30] Foreign Application Priority Data

Jan. 23, 1997 [JP] Japan ................................. 9-010269

[51] Int. Cl.⁶ .............................................. G01N 23/223
[52] U.S. Cl. ................................................. 378/46; 378/49
[58] Field of Search ................................. 378/44, 45, 46, 378/49, 90, 81

[56] References Cited

U.S. PATENT DOCUMENTS

| | | | |
|---|---|---|---|
| 4,959,848 | 9/1990 | Parobek ................................. | 378/46 |
| 4,988,872 | 1/1991 | Nagatsuka et al. ..................... | 250/310 |
| 5,497,008 | 3/1996 | Kumakhov ............................. | 250/505.1 |
| 5,912,940 | 6/1999 | O'Hara .................................. | 378/82 |

FOREIGN PATENT DOCUMENTS 0 766 083 A2   4/1991   European Pat. Off. .

7-35709   2/1995   Japan .

*Primary Examiner*—David P. Porta
*Attorney, Agent, or Firm*—Majestic, Parsons, Siebert & Hsue P.C.

[57] ABSTRACT

A fluorescent x-ray spectrometer, which can be used selectably both as a wavelength-dispersion type and an energy-dispersion type, includes an irradiation chamber and a detection chamber provided with both a first detector and a second detector respectively for detecting wavelength-type and energy-type dispersion. A sample disposed in the irradiation chamber is exposed to excitation x-ray and generates fluorescent x-ray which is introduced into the detection chamber along an incident optical path defined by a Soller slit and is made incident on a dispersing element. For detecting wavelength-type dispersion, dispersed x-ray is received by the first detector. For detecting energy-type dispersion, the dispersing element is retracted from the incident optical path such that the incident x-ray from the irradiation chamber is directly received by the second detector, disposed on an extension of the incident optical path, without being dispersed by the dispersing element.

6 Claims, 2 Drawing Sheets

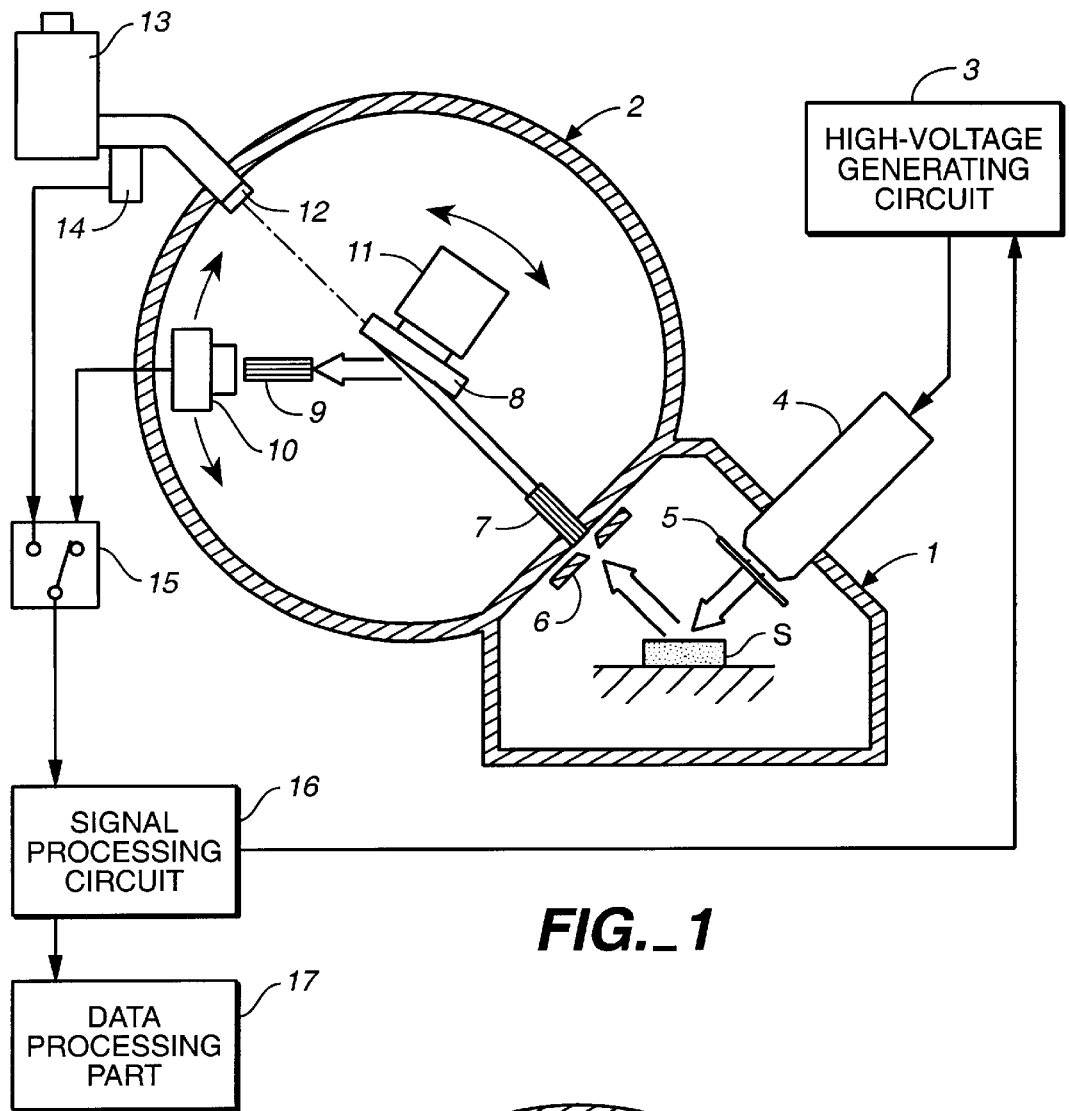
FIG._1
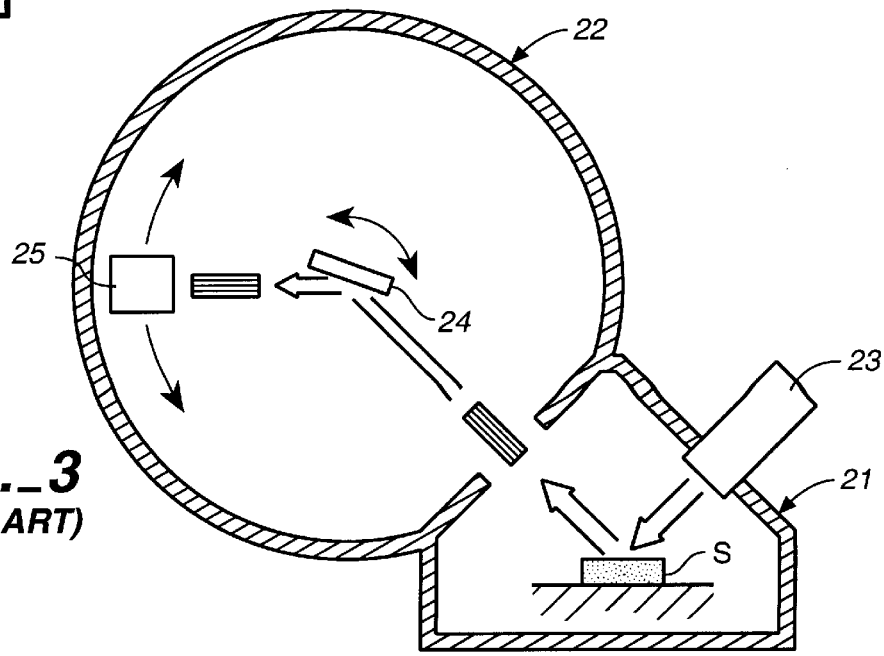
FIG._3
(PRIOR ART)

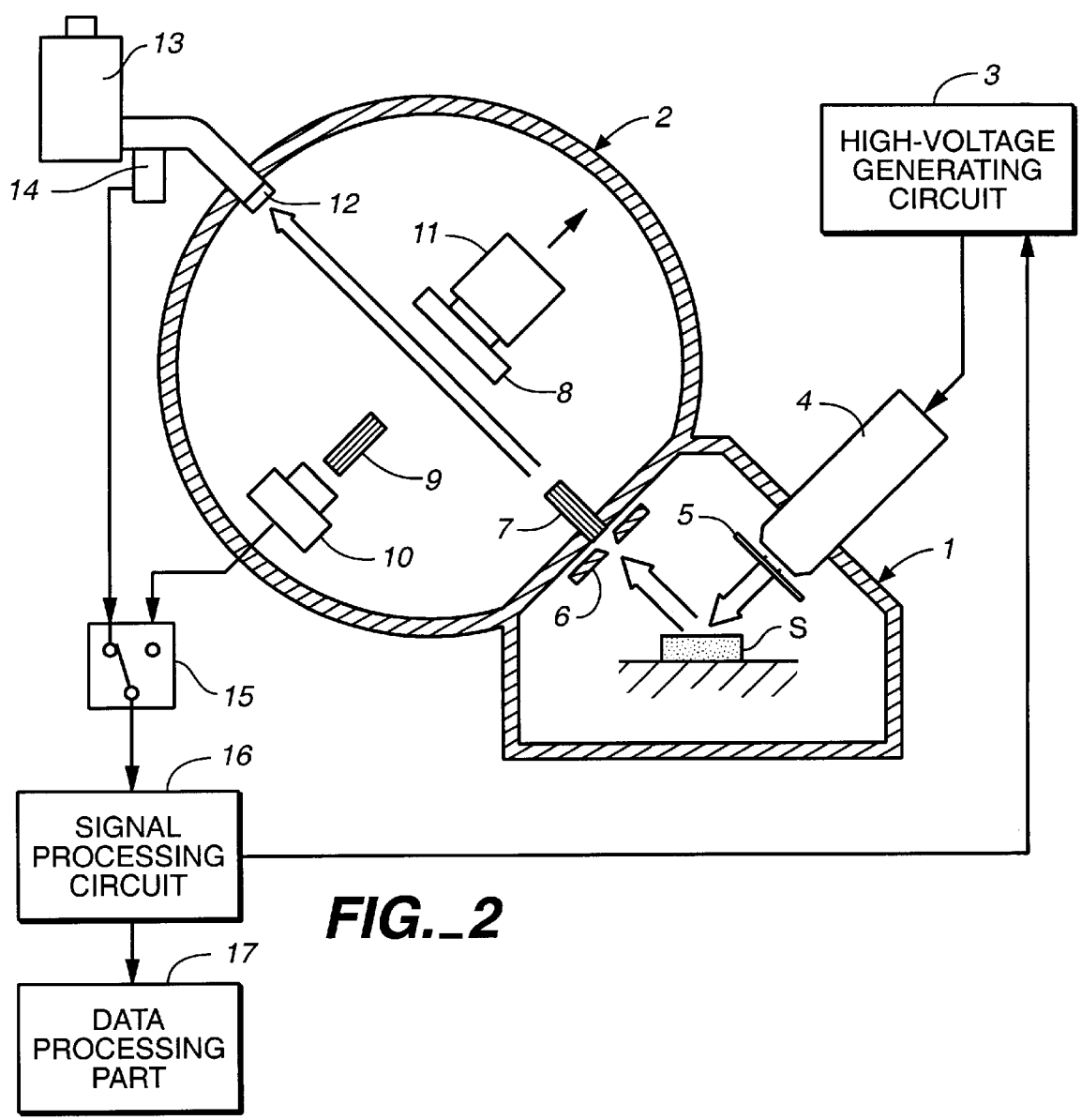
FIG._2
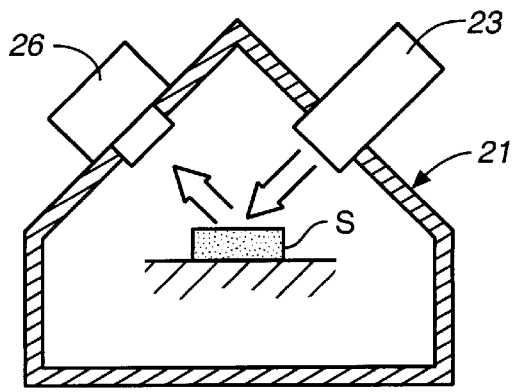
FIG._4
(PRIOR ART)

FLUORESCENT X-RAY SPECTROSCOPES

BACKGROUND OF THE INVENTION

This invention relates to fluorescent x-ray spectroscopes which can be used both as a wavelength-dispersion type and as an energy-dispersion type.

Fluorescent x-ray spectroscopes are for analyzing the constituent elements of a sample by irradiating the sample with excitation x-ray to thereby generate fluorescent x-ray and can be divided into the wave-dispersion type and the energy-dispersion type, depending on the method of detecting the fluorescent x-ray.

As shown in FIG. 3, a wavelength-dispersion type spectroscope comprises an irradiation chamber 21 and a detection chamber 22 provided next to each other, the irradiation chamber 21 being provided with an x-ray source 23 for irradiating a sample S set at a fixed position with a beam of excitation x-ray emitted therefrom. The fluorescent x-ray, which is generated by this irradiation of the sample S, is directed into the detection chamber 22. The detection chamber 22 contains therein at least a light-dispersing means, such as a dispersing element 24, and a detector 25 corresponding thereto such that the fluorescent x-ray introduced into the detection chamber 22 is dispersed by the dispersing element 24 into different wavelength components to be detected by the detector 25. The dispersing element 24 and the detector 25 are so controlled that the detector 25 will rotate by an angle of 2θ as the dispersing element 24 is rotated by θ such that fluorescent x-ray can be scanned over all its range of wavelength.

In the case of a spectroscope of the energy-dispersion type, as shown in FIG. 4, an x-ray source 23 and a detector 26 corresponding to its energy-dispersion are attached to its irradiation chamber 21. The fluorescent x-ray, which is generated inside this irradiation chamber 21 from the sample S by the irradiation of the excitation x-ray from the source 23, is not dispersed, and all its components are taken in by the detector 26 which is adapted to detect it at each of its energy levels.

Spectroscopes of each of these two types have their own advantages and disadvantages. The wavelength-dispersion type provides a better resolution and is capable of distinguishing individual elements even if they are at mutually near-by wavelength regions, but the angles of the dispersing element 24 and the detector 25 must be varied correspondingly for effecting a scan when elements scattered over a wide wavelength region are to be analyzed. This takes a relatively long period of time, and it is a disadvantage if a quick analysis is desired. The energy-dispersion type, on the other hand, can complete an analysis very quickly, say, within a few seconds or within a few minutes, even if the fluorescent x-ray is spread over a wide wavelength range because the spectrum of such a ray can be analyzed at the same time. It is therefore suitable for a quick analysis, but since there is a limit to the counting rate of the intensity of the fluorescent x-ray, it is difficult to carry out the analysis of a very small amount of an element.

For this reason, a sacrifice had to be made either in terms of the time of analysis or the accuracy of analysis when a prior art device was used. In other words, there were frequently situations where the primary object of analysis could not be accomplished. If devices of both types are to be made available, on the other hand, not only is it costly to be so prepared but also it is cumbersome to set and reset a sample from one device to another.

SUMMARY OF THE INVENTION

It is therefore an object of this invention to provide a fluorescent x-ray spectroscope which can be used both as a wavelength-dispersion type and as an energy-dispersion type such that an analysis of either type can be carried out effectively.

A fluorescent x-ray spectroscope embodying this invention, with which the above and other objects can be accomplished, may be characterized as comprising an irradiation chamber and a detection chamber adjacent each other such that a part of fluorescent x-ray generated in the irradiation chamber by irradiating excitation x-ray on a sample disposed therein is introduced into the detection chamber along an incident optical path. A dispersing element and a first detector corresponding thereto are disposed inside the detection chamber such that dispersed x-ray can be detected according to the wavelength. The dispersing element is adapted to be retracted from the incident optical path such that the incident fluorescent x-ray entering the detection chamber can be directly received by a second detector for the detection of x-ray energy. Thus, a single spectroscope can be used for detection of two different kinds.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a schematic structural diagram of a fluorescent x-ray spectroscope when it is being used as a spectroscope of a wavelength-dispersion type;

FIG. 2 is a schematic structural diagram of the fluorescent x-ray spectroscope of FIG. 1 when it is being used as a spectroscope of an energy-dispersion type;

FIG. 3 is a schematic structural diagram of a prior art fluorescent x-ray spectroscope of a wavelength-dispersion type; and FIG. 4 is a schematic structural diagram of a prior art fluorescent x-ray spectroscope of an energy-dispersion type.

Throughout herein, like elements may be indicated by the same symbols even if they are components of different devices and may not be repetitiously explained what they are.

DETAILED DESCRIPTION OF THE INVENTION

The invention is described next by way of an example with reference to FIGS. 1 and 2 wherein numerals 1 and 2 respectively indicate an irradiation chamber and a detection chamber provided adjacent each other. The irradiation chamber 1 is where fluorescent x-ray is generated from a sample S. There is attached thereto an x-ray tube 4, serving as a source of excitation x-ray and adapted to be activated by a high-voltage generating circuit 3 serving as a source of excitation x-ray. A sample S is adapted to be set at a specified position inside the irradiation chamber 1. A filter 5 is set in front of the x-ray tube 4.

The detection chamber 2 is where the fluorescent x-ray generated inside the irradiation chamber 1 is taken in and detected. An optical stop 6 for limiting the visual field is provided such that only a limited portion of the fluorescent x-ray will pass therethrough to enter the interior of the detection chamber 2. A first Soller slit 7 serving as an inlet, a dispersing element 8 serving as dispersing means for dispersing the fluorescent x-ray according to the wavelength, a second Soller slit 9 serving as an outlet and an x-ray detector 10 are provided inside the detection chamber 2. The dispersing element 8 is supported by a supporting member 11 on the optical path of the incident fluorescent x-ray through the first Soller slit 7 and is thereby adapted to receive it. The detector 10 is positioned so as to correspond to the fluorescent x-ray which has been dispersed. More specifically, a scintillation counter or a proportional counter tube may be used for this purpose. The wavelength-dispersion detector 10 and the second Soller slit 9 are supported so as to rotate by an angle of 2θ when the dispersing element 8 rotates by θ (in the direction of the arrows in FIG. 1). Means for effecting such coordinated rotary motions are known and are not shown in the drawings.

The present invention is characterized wherein the dispersing element 8, which serves to block the incident optical path of the fluorescent x-ray inside the detection chamber 2, is capable of being retracted from this incident optical path, as shown in FIG. 2. The retraction of the dispersing element 8 may be effected either by a retracting motion of the supporting member 11 (schematically indicated by an arrow in FIG. 2). If the supporting member is an exchanger of the type disclosed, for example, in Japanese Patent Publication Tokkai 7-218456 adapted to intermittently rotate a plate carrying thereon a plurality of dispersing elements, one of the positions for a dispersing element may be left unoccupied such that the same effect as retracting the supporting member can be obtained by rotating the plate such that the incoming x-ray will pass through this unoccupied position.

As for the detector 10 and the second Soller slit 9, it is to be noted that there is no need to provide any particular means for specifically retracting them from the incident optical path of the fluorescent x-ray because they can be moved away from the optical path of the incident fluorescent x-ray merely by adjusting their angles of rotation, as can be seen in FIG. 2.

Means for retracting, such as an exchanger as referred to above, may also be provided to the first Soller slit 7 in order to improve the sensitivity.

On the outer wall of the detection chamber 2, there is provided an x-ray detector 12 of the energy-dispersion type which may be a semiconductor detector such as a lithium-draft silicon detector. This detector 12 is at a position on the line which is an extension of the optical path of the incident fluorescent x-ray into the detection chamber 2 and opposite from the first Soller slit 7 such that the incident fluorescent x-ray will be directly received thereby if it is not blocked, say, by the dispersing element 8. A preamplifier 14 for the energy-dispersion detector 12 is disposed outside the outer wall of the detection chamber 2, and a cooler 13 is provided to cool the detector 12 as well as its preamplifier 14 by means of liquid nitrogen.

A signal switching circuit 15 is provided on the output side of the two detectors 10 and 12 such that output signals from the wavelength-dispersion and energy-dispersion detectors 10 and 12 can be selectably transmitted to a signal processing circuit 16. Output signals from the signal processing circuit 16 are transmitted to a data processing part 17 for analyzing the data contained in the signal received from the signal processing circuit 16.

When the fluorescent x-ray spectroscope thus structured is used as a detector of a wavelength-dispersion type, the dispersing element 8 is preliminarily positioned as shown in FIG. 1 on the incident optical path of the fluorescent x-ray and the switching circuit 15 is preset so as to connect the wavelength-dispersion detector 10 to the signal processing circuit 16. With preparations thus made, the sample S inside the irradiation chamber 1 is exposed to the excitation x-ray from the x-ray tube 4 with its tube current output kept at a constant level. As the fluorescent x-ray is generated from the sample S by this irradiation, a portion of this generated fluorescent x-ray is introduced into the detection chamber 2 and is made into a parallel beam by passing through the first Soller slit 7 and incident on the dispersing element 8. This incident beam is thereby dispersed into different wavelength components and detected by the corresponding wavelength-dispersion detector 10, which is caused to rotate by an angle of 2θ while the dispersing element 8 rotates by θ, as explained above, such that the entire range of wavelength is scanned.

The output signals from the wavelength-dispersion detector 10 are received through the switching circuit 15 by the signal processing circuit 16 such that data on the x-ray intensity of each wavelength component are obtained. Analysis of the sample S is carried out on the basis of these intensity data.

When this fluorescent x-ray spectroscope is used as a detector of an energy-dispersion type, the dispersing element 8 is preliminarily oriented as shown in FIG. 2 at zero-angle with respect to the direction of the incident optical path of the fluorescent x-ray and is then retracted away from the incident optical path such that no part of it will block the x-ray on the incident optical path. The wavelength-dispersion detector 10 and the second Soller slit 9 are also rotated so as to be at a position 90° from the incident optical path and to be retracted therefrom. The switching circuit 15 is further preset so as to connect the energy-dispersion detector 12 to the signal processing circuit 16. With preparations thus made, the sample S inside the irradiation chamber 1 is exposed to the excitation x-ray from the x-ray tube 4 with its tube current output controlled according to the characteristics of the detector 12.

Inside the detection chamber 2, since there is nothing that blocks the incident fluorescent x-ray beam, it is not dispersed and is directly received by the energy-dispersion detector 12. Thus, a signal indicative of the energy level of the incident x-ray is obtained, and it is transmitted through the switching circuit 15 to the signal processing circuit 16. Processes such as energy selection are carried out such that data as in the case of wavelength-dispersion may be obtained.

The invention has been described above with reference to only one embodiment but this is not intended to limit the scope of the invention. Many modifications and variations are possible within the scope of this invention. Although a switching circuit 15 is provided in the example shown in FIGS. 1 and 2 such that output signals from the two detectors 10 and 12 can be selectably transmitted to the signal processing circuit 16, each of the two detectors 10 and 12 may be provided with its own signal processing circuit.

In summary, a spectroscope according to this invention can be used as a detector of either of two different types. It can be used as a detector of an energy-dispersion type when it is desired to quickly ascertain the elemental composition of a sample but can also be used as a detector of a wavelength-dispersion type when it is desired to analyze even those components which are contained by only very small amounts. Moreover, the switch-over can be carried out very easily merely by moving a few of the components inside the detection chamber without the need to reset the sample. Thus, analyses of two kinds can be carried out within a short period of time. After two kinds of analyses are thus carried out and two sets of data are obtained, furthermore, it may be possible to make up for any insufficiency in one set of data by using the other set of data. Reliability of analysis can thus be improved. It now goes without saying that a spectroscope according to this invention can be produced more inexpensively than if detectors of both types are to be provided since many of the components such as the x-ray tube and a gas exhaust system can be used for both types of operation.

What is claimed is:

1. A fluorescent x-ray spectrometer comprising:

an irradiation chamber for causing fluorescent x-ray to be generated by irradiating excitation x-ray on a sample disposed therein;

a detection chamber adjacent said irradiation chamber, an incident optical path being defined inside said detection chamber for a part of said fluorescent x-ray introduced from said irradiation chamber into said detection chamber, said detection chamber containing therein a dispersing element and a first detector corresponding to said dispersing element for detecting x-ray dispersed by said dispersing element, said dispersing element being retractable inside said detection chamber from said incident optical path; and a second detector for detecting x-ray energy disposed on an extension of said incident optical path.

2. The fluorescent x-ray detector of claim 1 further comprising a signal processing circuit for processing signals received selectively from said first detector or from said second detector and a switching circuit for causing signals selectively from said first detector or said second detector to be transmitted to said signal processing circuit.

3. The fluorescent x-ray detector of claim 2 further comprising a data processing part connected to said signal processing circuit for analyzing data contained in signals received from said signal processing circuit.

4. The fluorescent x-ray detector of claim 1 further comprising a first Soller slit and a second Soller slit, both disposed inside said detection chamber, said first Soller slit being disposed between said irradiation chamber and said dispersing element and serving to define said incident optical path, said second Soller slit being disposed between said dispersing element and said first detector.

5. The fluorescent x-ray detector of claim 2 further comprising a first Soller slit and a second Soller slit, both disposed inside said detection chamber, said first Soller slit being disposed between said irradiation chamber and said dispersing element and serving to define said incident optical path, said second Soller slit being disposed between said dispersing element and said first detector.

6. The fluorescent x-ray detector of claim 3 further comprising a first Soller slit and a second Soller slit, both disposed inside said detection chamber, said first Soller slit being disposed between said irradiation chamber and said dispersing element and serving to define said incident optical path, said second Soller slit being disposed between said dispersing element and said first detector.

* * * * *